United States Patent [19]

Mayer et al.

[11] 4,308,195

[45] Dec. 29, 1981

[54] EPOXIDE RESINS CONTAINING PHENOL GROUPS, THEIR MANUFACTURE AND THEIR USE

[75] Inventors: Norbert Mayer, Gablingen; Gerhard Pfahler, Augsburg; Franz Scheidl, Gersthofen, all of Fed. Rep. of Germany

[73] Assignee: Hoechst Aktiengesellschaft, Fed. Rep. of Germany

[21] Appl. No.: 143,089

[22] Filed: Apr. 23, 1980

[30] Foreign Application Priority Data

Apr. 26, 1979 [DE] Fed. Rep. of Germany ....... 2916877

[51] Int. Cl.³ .................. C08K 5/13; C08L 23/06
[52] U.S. Cl. .................. 260/45.8 A; 260/45.8 NT; 260/45.8 NZ; 260/348.58; 260/348.62; 260/348.12; 544/215; 544/221; 548/312; 525/120; 528/100
[58] Field of Search ............ 260/348.58, 348.62, 260/45.8 A, 45.8 NT, 45.8 NZ, 348.12; 544/221, 215; 548/312; 525/120; 528/100

[56] References Cited

U.S. PATENT DOCUMENTS 3,496,128  2/1970  Casey et al. .................. 260/23

FOREIGN PATENT DOCUMENTS 1325974  8/1973  United Kingdom.

*Primary Examiner*—Earl A. Nielsen
*Attorney, Agent, or Firm*—Connolly and Hutz

[57] ABSTRACT

The present invention relates to epoxide resins containing phenol groups and to homo-oligomers thereof of the structure

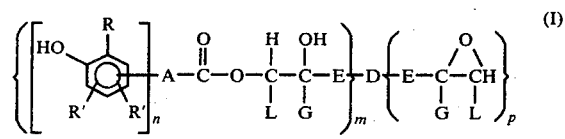

that are obtained by reacting phenolcarboxylic acids with one epoxide equivalent of a polyepoxide. The new compounds are difficultly volatile and resistant to migration and can be used as stabilizers in synthetic polymers, in particular in poly-α-olefins.

4 Claims, No Drawings

EPOXIDE RESINS CONTAINING PHENOL GROUPS, THEIR MANUFACTURE AND THEIR USE

As is known, phenolic antioxidants have been added for a long time to plastics, in particular polyolefins, in order to delay their degradation under the influence of atmospheric oxygen and heat. The effective period of long-term stabilization is limited, inter alia, by the fact that the stabilizer migrates or is dissolved out of the plastic. There has been no lack of attempts to reduce the extractability of the additives. Thus is has been suggested, for example, to mix into the plastic powder phenoldiazo compounds which decompose during processing, with evolution of nitrogen, into carbenes which undergo an addition reaction with the hydrocarbon chain of the plastic [Polymer Letters Edition Vol. 11, pages 357-361 (1973)]. This process has the disadvantage that the nitrogen formed leads to the formation of bubbles in the plastic. The same objection can be raised against sulfonylazide antioxidants and against azidoformyl antioxidants (German Offenlegungsschrift No. 2,733,657 and German Offenlegungsschrift No. 2,636,136, respectively).

A further class of phenolic antioxidants is constituted by polymers of sterically hindered phenols which have vinyl groups in a position adjacent to the aromatic nucleus (for example U.S. Pat. No. 4,028,342 and Japanese Pat. No. 77,050-048). The serious disadvantage of this class of compounds is that the polymers tend to break up again into the volatile monomeric starting products under the considerable heat to which they are exposed during the processing of the plastic.

O,O'-crosslinked, polymeric phenolic antioxidants containing phenylsulfonic acid groups in the polymer structure have also already been suggested (German Offenlegungsschrift No. 2,716,811).

Such antioxidants can have a certain importance for Cu-complexing in cable sheathing, but they are, in general, certainly not suitable for stabilizing polyolefins, since the action of phenylsulfonic acid on phenols at the high temperatures at which polyolefins are processed leads to discoloration phenomena.

Polymeric phenol esters in which the linking of the monomer units is brought about by esterifying the phenolic OH group with polybasic acids are also already known as antioxidants (German Offenlegungsschrift No. 2,715,589). The disadvantage of this class of compounds is that, as a result of the formation of the ester, the phenol grouping which is effective as an antioxidant is in part blocked and thus prevented from developing its full effectiveness.

Finally, polymeric phenolic antioxidants which are prepared by Ziegler polymerization of unsaturated alcohols followed by transesterification with phenol alkanecarboxylic acid esters (German Auslegeschrift No. 2,119,701) have also been described. This route of synthesis is involved and complicated.

While the low-molecular carbene precursors mentioned initially can indeed be distributed homogeneously in the plastic, but have the disadvantages described, the polymeric antioxidants quoted can no longer be homogeneously dispersed at a low concentration in the plastic, because of their high molecular weight. The result of this is that either it is necessary to employ high concentrations of stabilizer, which is uneconomic, or a stabilization has to be accepted which is not very satisfactory, relative to the state of the art, if value is set on high resistance to migration of the stabilizer employed.

There is, therefore, a need for stabilizers which have, on the one hand, a molecular weight sufficiently small to achieve homogeneous distribution in the plastic, but which, on the other hand, in part still contain reactive groups which, under the conditions of plastics processing, contribute towards an increase in the molecular weight and thus to an improvement in the resistance to migration.

It has been found that certain epoxide resins containing phenol groups fulfil, surprisingly, the requirements set.

The present invention relates, therefore, to epoxide resins containing phenol groups and homooligomers thereof of the general formula (I)

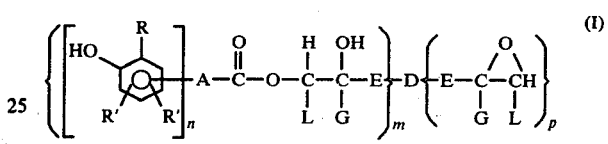

in which R, R' and R" independently of one another denote H or $C_1$ to $C_4$ alkyl, n should be 1 or 2 and A is a chemical bond or ($\alpha$) the radical of a straight-chain or branched, unsubstituted or phenyl-substituted alkane having 1 to 20 C atoms, or ($\beta$) the radical of a cycloaliphatic alkane which has 5 to 12 C atoms and is unsubstituted or substituted by $C_1$ to $C_5$ alkyl, or ($\gamma$) a phenyl or naphthyl radical unsubstituted or substituted by $C_1$ to $C_{12}$ alkyl, E represents a $CH_2$ group, G represents an H atom or a $CH_3$ group and L represents an H atom, or E and L, conjointly with the C atoms linking them, form a cycloalkyl radical which has 5 to 12 C atoms and which can also be alkyl-substituted, and D should be oxygen or a radical of the formula

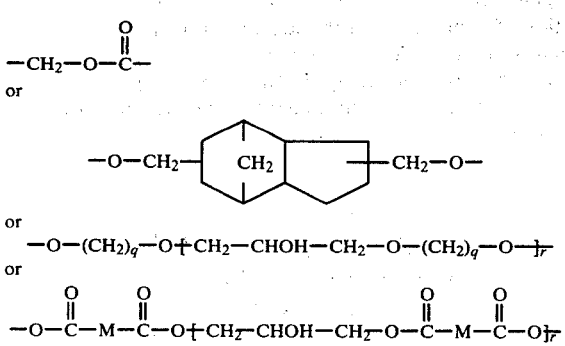

or

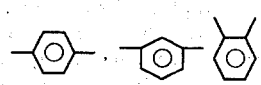

or

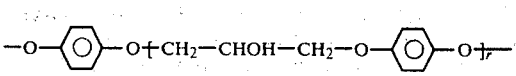

or

-continued

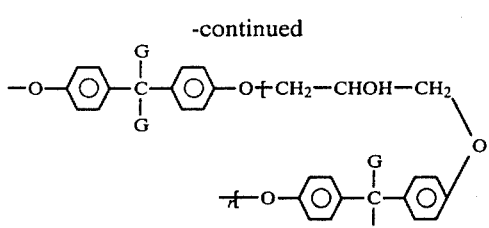

in which q = 2 to 10 and r = 0 to 10, or

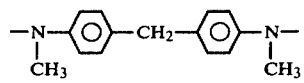

or

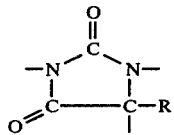

or

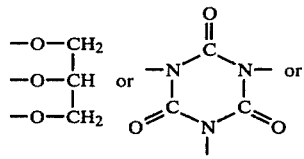

or

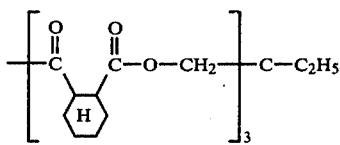

or

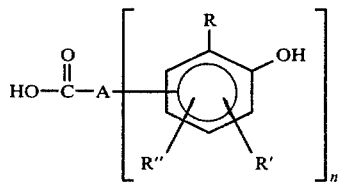

and m denotes 1, 2 or 3 and p denotes 0, 1 or 2, with the limitation that p+m is not greater than 3.

The invention also relates to a process for the preparation of compounds of the structure (I) and their use as stabilizers in synthetic polymers.

The phenolic grouping illustrated in the general formula (I) is derived from a phenolcarboxylic acid of the structure $$HO-\overset{O}{\underset{\|}{C}}-A-\left[\begin{array}{c} R \\ \diagup\diagdown \\ \text{(ring)} \\ R'' \quad R' \end{array} OH\right]_n$$

wherein A, R, R', R" and n have the meaning indicated above. Preferred examples of such phenolcarboxylic acids in which n=1 are salicylic acid and 3,5-di-tert.-butyl-4-hydroxyphenylpropionic acid, and also p-hydroxybenzoic and m-hydroxybenzoic acids, 3,5-di-tert.-butyl-4-hydroxybenzoic acid, 3,5-di-tert.-butyl-4-hydroxyphenylacetic acid and also 2,4-di-tert.-butyl-3-hydroxyphenyl-6-methylbenzoic acid and modification products thereof, which are described in greater detail, for example, in German Offenlegungsschrift No. 2,445,306.

Phenolcarboxylic acids in which n=2 are bishydroxyphenylcarboxylic acids, which are known, for example, from German Offenlegungsschrift No. 2,544,014.

Examples of suitable acids are 3,3-bis-(3'-tert.-butyl-4'-hydroxyphenyl)-butanoic acid, bis-(3-tert.-butyl-4-hydroxyphenyl)-acetic acid, 2,2-bis-(3'-tert.-butyl-4'-hydroxyphenyl)-cyclohexane-1-carboxylic acid or 2,2-bis-(3'-tert.-butyl-4'-hydroxyphenyl)-cyclohexyl-1-propionic acid. In this preferred class of compounds, special mention should be made of bis-(3-tert.-butyl-4-hydroxyphenyl)-acetic acid, 3,3-bis-(3'-tert.-butyl-4'-hydroxyphenyl)-butanoic acid and 4,4-bis-(3'-tert.-butyl-4'-hydroxyphenyl)-pentanoic acid.

The substances according to the invention are obtained by reacting phenolcarboxylic acids with epoxide compounds. Thus an addition reaction is carried out between, for example, 1 or 2 moles of phenolcarboxylic acid and diglycidyl ether, bis-(glycidyloxymethyl)-tricyclododecane, alkylenediol diglycidyl ethers, α,ω-bis-glycidylalkylenediol glycerol polyethers, diglycidyl esters, di-β-methylglycidyl esters of aliphatic, cycloaliphatic or aromatic dicarboxylic acids which optionally contain alkyl branches, α,ω-bis-glycidyldicarboxylic acid glycerol polyesters, resorcinol or hydroquinone diglycidyl ether, α,ω-bis-glycidylhydroquinone glycerol polyethers, bisphenol F diglycidyl ether or bisphenol A diglycidyl ether, α,ω-diglycidyl glycerol polyethers thereof, N,N'-bis-glycidyl-N,N'-dimethylaminodiphenylmethane or N,N'-bis-glycidylhydantoins.

It is also possible to react one, two or three moles of phenolcarboxylic acid with one mole of glycerol triglycidyl ether or triglycidyl isocyanurate or 2,4,6-tris-epoxypropyltriazine or trimethylolpropane tris-(2,3-epoxypropylhexahydrophthalate), or to carry out an addition reaction between one or two moles of phenolcarboxylic acid and, for example, bis-(2,3-epoxycyclopentyl) ether or 3,4-epoxycyclohexylmethyl 3,4-epoxycyclohexanecarboxylate or bis-(3,4-epoxy-6-methylcyclohexylmethyl) adipate or bis-(3,4-epoxycyclohexylmethyl) adipate.

In the reaction the free phenolcarboxylic acids are generally reacted with the epoxide compounds at 50° to about 200° C., preferably at 80° to 130° C. The reaction can be carried out either in the absence of a solvent or in the presence of inert, aromatic or aliphatic solvents, such as xylene, toluene or diisobutyl ketone, analogously to a process described in German Offenlegungsschrift No. 2,449,847. If the process is carried out without a solvent, the reaction can be carried out in mixers or kneaders or on rolls.

The preferred reaction is that of phenolcarboxylic acids with commercially available diepoxide and polyepoxide compounds, the preparation of which is described in detail in the literature, for example in Houben-Weyl 14/2 (1963) pages 462 et seq. or in "Praktikum der Makromolekularen Organischen Chemie" ("Practical Work in Macromolecular Organic Chemistry") Hüthig-Verlag Heidelberg, 1966, page 218 et seq..

Examples of such polyepoxide compounds are polyglycidyl ethers or poly-β-methylglycidyl ethers of poly-β-methylglycidyl ethers of polyhydric alcohols, such as polyethylene glycols, polypropylene glycols or 2,2-bis-(4'-hydroxycyclohexyl)-propane, of polyhydric phenols, such as 2,2-bis-(4'-hydroxyphenyl)-propane, 2,2-bis-(4'-hydroxy-3',5'-dibromophenyl)-propane, bis- (4-hydroxyphenyl) sulfone or 1,1,2,2-tetrakis-(4-hydroxyphenyl)-ethane, and also polyglycidyl esters or poly-β-methylglycidyl esters of polycarboxylic acids, for example phthalic acid diglycidyl ester, isophthalic acid diglycidyl ester, $\Delta^4$-tetrahydrophthalic acid diglycidyl ester, hexahydrophthalic acid diglycidyl ester, glutaric acid diglycidyl ester, adipic acid diglycidyl ester, sebacic acid diglycidyl ester or alkyl-substituted dicarboxylic acid di-(β-methylglycidyl) esters, such as are described, for example, in German Auslegeschrift No. 1,942,836, triglycidyl isocyanurate, N,N'-diglycidyl-5,5-dimethylhydantoin or epoxide compounds which are obtained from the dehydrohalogenation of the reaction products formed from an epihalogenohydrin or β-methylepihalogenohydrin and primary or secondary amines, such as aniline or 4,4'-diaminodiphenylmethane; also alicyclic compounds containing several epoxide groups, such as vinylcyclohexene diepoxide, dicyclopentadiene diepoxide, ethylene glycol bis-(3,4-epoxytetrahydrodicyclopentadien-8-yl) ether, 3',4'-epoxycyclohexylmethyl, 3,4-epoxycyclohexanecarboxylate, 3',4'-epoxy-6'-methylcyclohexylmethyl 3,4-epoxy-6-methylcyclohexanecarboxylate, bis-(2,3-epoxycyclopentyl) ether, 3-(3',4'-epoxycyclohexyl)-2,4-dioxaspiro-(5,5)-9,10-epoxyundecane, 3,4-epoxyhexahydrobenzene-3',4'-epoxy-1',1'-bis-(hydroxymethyl)-cyclohexane, bis-(3,4-epoxy-6-methylcyclohexyl) adipate or bis-(3,4-epoxycyclohexylmethyl) adipate.

If desired, it is possible to employ one or more of the polyepoxide compounds listed, if appropriate also as a mixture with so-called reactive thinners, such as, for example, styrene oxide, butyl glycidyl ether, isooctyl glycidyl ether, phenyl glycidyl ether, cresyl glycidyl ether or glycidyl esters of synthetic aliphatic monocarboxylic acids which are highly branched and mainly tertiary.

It is also possible subsequently to increase the molecular weight of the resulting addition reaction products which still contain epoxide groups and which have been formed from polyepoxide and phenolcarboxylic acid. This is achieved by reacting them with so-called curing agents. Basic or acid compounds are suitable for this purpose, for example amines or amides, such as aliphatic, cycloaliphatic or aromatic primary, secondary and tertiary amines, such as ethanolamine, ethylenediamine, hexamethylenediamine, trimethylhexamethylenediamine, diethylenetriamine, triethylenetetramine, tetraethylenepentamine, 2,2,6,6-tetramethyl-4-aminopiperidine, 2,2,6,6-tetramethyl-4-hydroxypiperidine, N,N-dimethylpropylene-1,3-diamine, N,N-diethylpropylene-1,3-diamine, bis-(4-amino-3-methylcyclohexyl)-methane, 3,5,5-trimethyl-3-(aminomethyl)-cyclohexylamine ("isophoronediamine"), Mannich bases, such as 2,4,6-tris-dimethylaminomethyl)-phenol, m-phenylenediamine, p-phenylenediamine, bis-(4-aminophenyl)-methane, bis-(4-aminophenyl) sulfone, m-xylylenediamine or N-(2-aminoethyl)-piperazine.

Acid curing agents which may be mentioned are, inter alia, polybasic carboxylic acids and anhydrides thereof, for example phthalic anhydride, $\Delta^4$-tetrahydrophthalic anhydride, hexahydrophthalic anhydride, 4-methylhexahydrophthalic anhydride, 3,6-endomethylene-$\Delta^4$-tetrahydrophthalic anhydride, 4-methyl-3,6-endomethylene-$\Delta^4$-tetrahydrophthalic anhydride (=methylnadic anhydride), 3,4,5,6,7,7-hexachloro-3,6-endomethylene-$\Delta^4$-tetrahydrophthalic anhydride, succinic anhydride, adipic anhydride, azelaic anhydride, sebacic anhydride, maleic anhydride, dodecylsuccinic anhydride or pyromellitic anhydride or mixtures of such anhydrides.

The reaction with the polycarboxylic acid anhydrides mentioned can be accelerated by adding basic compounds, such as alkali metal alcoholates, tertiary amines, salts thereof or quaternary ammonium compounds. Examples which may be mentioned are benzyldimethylaniline, 4-aminopyridine, 4-(dimethylamino)-pyridine and especially alkali metal methylates, ethylates or isopropylates. Acid compounds, such as, for example, phosphorous or phosphoric acid, are also suitable. The quantities of catalyst are 0.001 to 1% by weight, relative to epoxide.

An advantage of the class of substances according to the invention which should not be underestimated is that the epoxide compounds used as the starting materials are manufactured on a large industrial scale and are extensively used in the lacquer industry, for example for lacquering tin cans. Combined with the phenolcarboxylic acids, which are readily accessible in a simple manner from cheap starting materials, and the manufacturing process according to the invention, which proceeds smoothly, the polymeric stabilizers according to the invention can thus be prepared at a low price.

In addition to the fact that they can be easily prepared from readily accessible starting materials, the high stability to discoloration of the stabilizers according to the invention when employed in plastics should also be singled out. This is surprising, and was not to be foreseen, especially in the case of the phenolcarboxylic acid esters of glycerol derivatives. As is known from the chemistry of fats, glycerol carboxylic acid esters tend to form colored decomposition products when exposed to heat. It is all the more surprising that the compounds according to the invention, of a similar structure, have been better color properties than commercially available phenolic antioxidants.

The low volatility of the stabilizers according to the invention should also be singled out. This is because, while the polymers initially mentioned of ethylenically unsaturated compounds have a tendency—as already mentioned—under the considerable heat to which they are exposed in the processing of plastics, to split up again into monomers, under these conditions the compounds according to the invention tend even to increase in molecular weight, since the epoxide groups still present in the oligomer can react with themselves and, if appropriate, also with added amines, carboxylic acids or carboxylic acid anhydrides, to give higher-molecular substances. This behaviour is particularly advantageous because prepolymeric antioxidants having a comparatively low molecular weight which is still optimal for homogeneous distribution in the plastic can in this way be homogeneously incorporated and distributed in the plastic during processing and can simultaneously react further, under the influence of the high processing temperature, to give higher-molecular stabilizers which are resistant to migration.

This advantageous behaviour of the substances according to the invention is not to be found in any of the stabilizer systems hitherto described and constitutes a considerable advance compared with the state of the art.

The epoxide resins according to the invention, containing phenol groups, are preferably prepolymers of a not excessively high molecular weight, say of an order of magnitude of 1,000 to 10,000, especially 2,000 to 5,000. They are obtained by an addition reaction between 0.01 to at most 1 mole of phenolcarboxylic acid with one epoxide equivalent of a polyepoxide compound, the reaction conditions being chosen so that the formation of crosslinked, highly polymeric reaction products is avoided. This is achieved, for example, by diluting the reactants with a solvent, by means of a low reaction temperature of, say, 50° to 110° C. and, above all, by discontinuing the reaction in good time by reducing the temperature as soon as the precipitation of insoluble, crosslinked high polymers manifests itself—perhaps by the reaction batch becoming turbid.

The stabilizers according to the invention are distinguished by their high resistance to extraction. A high resistance of the stabilizer in the plastic against, in addition, extraction by oil-like and fat-like substances is of particular importance because, on the one hand, the intended protection of the plastic against oxidation is also retained in contact with oils and fats and, above all, because, in addition, the contamination with the stabilizers, which is extremely undesirable, of fat-containing and oil-containing foodstuffs which may be wrapped up in the plastic does not take place.

The epoxide resins, of the invention, containing phenol groups are outstandingly suitable for stabilizing synthetic polymers and copolymers of $C_2$ to $C_4$ α-olefins, preferably polyolefins, such as polybutadiene, polyisoprene and especially polyethylene and polypropylene, and also for polystyrene, polyacrylates and polymethacrylates, including the grades which are reinforced by glass fibers, asbestos and the like. They are used in quantities of 0.001 to 5.0, preferably 0.01 to 1.0,% by weight, relative to the polymer. They have a preferred field of application, above all, in cases where the plastic is exposed to media having an eluting action, such as oil, fat or organic solvents and also water, acids and alkali solutions.

If appropriate, other customary phenolic antioxidants are also added as co-stabilizers in the stabilization of polymers. The following examples may be mentioned from the large numbers of products suitable for this purpose: esters of 3,5-di-tert.-butyl-4-hydroxyphenyl-propionic acid or of 3,3-bis-(3'-tert.-butyl-4'-hydroxy-phenyl)-butyric acid. Alkaline earth metal salts of long-chain carboxylic acids, for example Ca stearate or Ca montanate, are used as pH stabilizers. In some cases it proves advantageous to add sulfur-containing co-stabilizers, for example lauryl or stearyl thiodipropionate or dioctadecyl sulfide or dioctadecyl disulfide. Examples of phosphorus-containing co-stabilizers which may be mentioned are phosphites, phosphinates and phosphonates, such as, say, distearyl-pentaerythrityl diphosphite, distearyl-β-hydroxytriacontylsorbityl triphosphite, tris-(2,4-di-tert.-butylphenyl) phosphite, diphenyl-4,4'-diphosphinic acid tetrakis-(2,4-di-tert.-butylphenyl) ester or the Ca or Ni salt of 3,5-di-tert.-butyl-4-hydroxybenzylphosphonic acid ethyl ester. Occasionally it is also advisable to employ, in addition to the co-stabilizers mentioned, light stabilizers; examples of these which may be mentioned are hydroxybenzophenones, benztriazoles or the piperidine stabilizers, especially the highly polymeric representatives of this class of substances.

The examples which follow are intended to illustrate the invention in greater detail.

EXAMPLE 1

Oligomers of glycerol bis-(2-hydroxy-3-[3',3'-di-(3"-tert.-butyl-4"-hydroxyphenyl)-butyroxy]-propyl) monoglycidyl triether

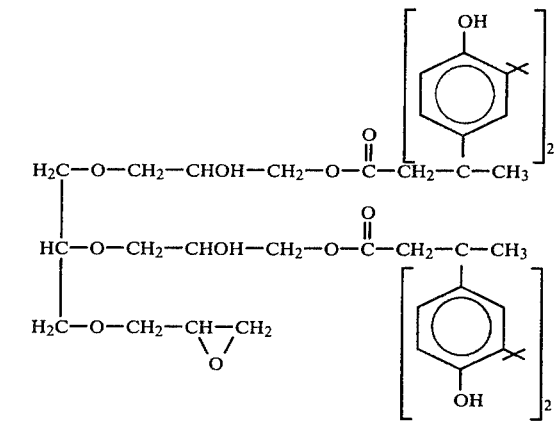

10 g (1/30 mole) of tris-glycidyl glycerol ether (obtained by the method of "Praktikum der Makromolekularen Organischen Chemie", Hüthig Verlag Heidelberg 1966, page 222), 25.3 g (2/30 mole) of 3,3-bis-(3'-tert.-butyl-4'-hydroxyphenyl)-butanoic acid (prepared in accordance with German Offenlegungsschrift No. 2,544,014) and 0.05 g of KOH in 50 ml of xylene are boiled under reflux for 4 hours. After this time 3,3-bis-(3'-tert.-butyl-4'-hydroxyphenyl)-butanoic acid can no longer be detected in a thin layer chromatogram. The solvent is then distilled off under a water pump vacuum. The residue which remains, a nearly colorless glass of flowing point/dropping point 100/109° C., has a molecular weight of 1,230, determined by vapor pressure osmometry (theoretical MW 1,061), which corresponds to a degree of polymerization of 1.16.

(a) 5 g of the product obtained are heat-treated at 200° C. for two hours. As a result of this procedure, the molecular weight increases to 2,800 and the flowing point/dropping point to 115/120° C.

(b) 5 g of the product obtained are mixed with 0.5 g of tetrahydrophthalic anhydride and the mixture is melted and heat-treated at 150° C. for one hour. This gives a product having a molecular mass of 3,140, which corresponds to a degree of polymerization of 2.6. The flowing point/dropping point has increased to 119/130° C.

(c) 5 g of the product are heat-treated with 0.5 g of terephthalic acid at 200° C. for two hours as indicated above. The product is insoluble in all solvents and is infusible.

EXAMPLE 2

Oligomers of glycerol mono-(2-hydroxy-3-[3',3'-di-(3"-tert.-butyl-4"-hydroxyphenyl)-butyroxy]-propyl) bis-glycidyl triether

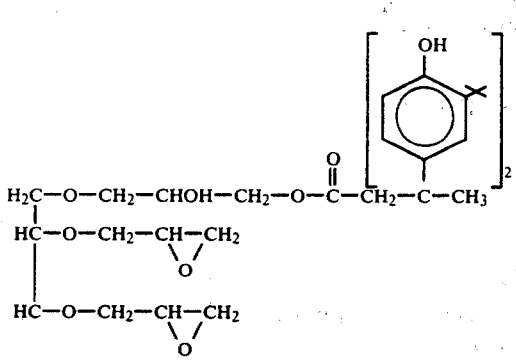

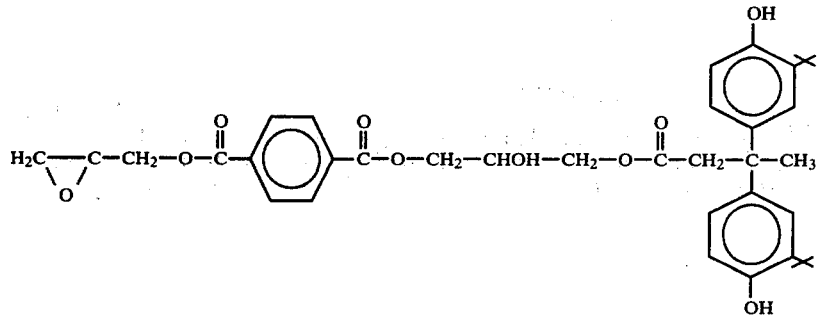

and o-tert.-butylphenol analogously to a method described in German Offenlegungsschrift No. 2,544,014) in 50 ml of xylene are boiled under reflux for five hours in the presence of 0.05 g of KOH, analogously to Example 1. After this time the phenolcarboxylic acid has reacted completely according to a thin layer chromatogram. Removal of the solvent leaves, as the residue, a colorless, glass-like resin having a molecular weight of 1,830, which corresponds to a degree of polymerization of approx. 1.7.

EXAMPLE 4

Oligomers of terephthalic acid monoglycidyl mono-(2-hydroxy-3-[3',3'-di-(3''-tert.-butyl-4''-hydroxy-phenyl)-butyroxy]-propyl) ester 27.8 g (0.1 mole) of terephthalic acid diglycidyl ester and 38.4 g (0.1 mole) of 3,3-bis-(3'-tert.-butyl-4'-hydroxyphenyl)-butanoic acid in 250 ml of xylene are boiled under reflux for three hours in the presence of a trace of KOH, analogously to Example 1. Removal of the solvent by evaporation gives 60 g of a brittle glass having a flowing point/dropping point of 116/123° C. and a MW of 955, which corresponds to a degree of polymerization of 1.4.

If 7.3 g of this product are heat-treated with 0.55 g of tetrahydrophthalic anhydride at 150° C. for one hour, a substance with a molecular weight of 1,540 is obtained, which corresponds to a degree of polymerization of 2.3. The flowing point/dropping point is 119/136° C.

10 g (1/30 mole) of tris-glycidyl glycerol ether, 12.7 g (1/30 mole) of 3,3-bis-(3'-tert.-butyl-4'-hydroxyphenyl)-butanoic acid and 0.05 g of KOH in 50 ml of xylene are boiled under reflux for 90 minutes.

Phenolcarboxylic acid is then no longer detectable in a thin layer chromatogram. The reaction mixture is neutralized with 0.5 ml of glacial acetic acid and the solvent is distilled off. This gives a glossy resin with a slight yellowish discoloration and a molecular weight of 2,240. Heat-treatment for 15 to 30 minutes at 200° C./vacuum increases the molecular weight to 2,410 to 2,510, which corresponds to a degree of polymerization of about 3 to 4.

EXAMPLE 3

Oligomers of glycerol bis-(2-hydroxy-3-[4',4'-di-(3''-tert.-butyl-4''-hydroxyphenyl)-pentanoyloxy]-propyl) glycidyl ether

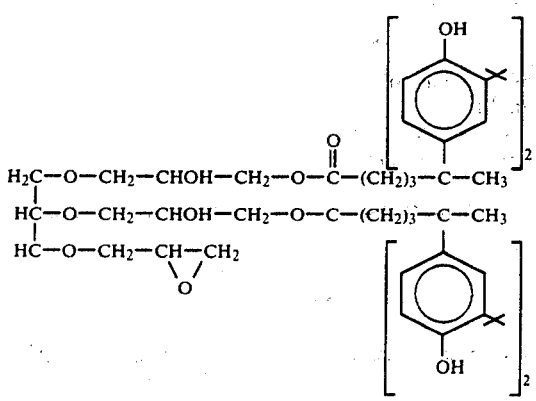

5 g (1/60 mole) of tris-glycidyl glycerol ether and 13.3 g (2/60 mole) of 4,4-bis-(3'-tert.-butyl-4'-hydroxyphenyl)-pentanoic acid (prepared from levulinic acid

EXAMPLE 5

Terephthalic acid 2-hydroxy-3-[3',3'-di-(3''-tert.-butyl-4''-hydroxyphenyl)-butyroxy]-propyl diester

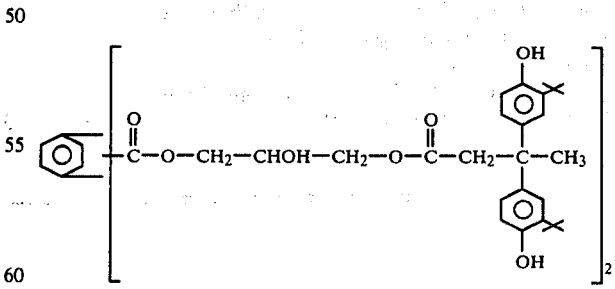

15.3 g (0.055 mole) of terephthalic acid diglycidyl ester and 38.4 g (0.10 mole) of 3,3-bis-(3'-tert.-butyl-4'-hydroxyphenyl)-butanoic acid in 250 ml of xylene are boiled under reflux for 24 hours in the presence of a trace of NaOH, analogously to Example 1. After adding a further 1.5 g of terephthalic acid diglycidyl ester, the mixture is boiled for a further four hours. The product remaining as residue after neutralization with a little glacial acetic acid and removing the solvent by evaporation has a flowing point/dropping point of 112/123° C. and a molecular weight of 1,160 (theory 1,074).

EXAMPLE 6

Oligomer of bisphenol A/bisphenol F monoglycidyl mono-(2-hydroxy-3-[3',3'-di-(3''-tert.-butyl-4''-hydroxyphenyl)-butyroxy]-propyl ether

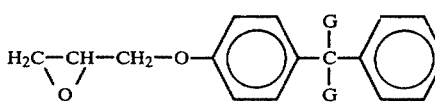
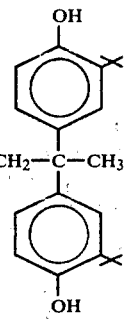

G = H, CH₃

18.3 g (0.05 mole) of a commercially available mixture consisting of approx. 70% of bisphenol A diglycidyl ether and 30% of bisphenol F diglycidyl ether [2,2-(4,4'-dihydroxydiphenyl)-dimethylmethane and 2,2-(4,4'-dihydroxydiphenyl)-methane, respectively]in 200 ml of dimethylformamide are added dropwise, in the course of two hours, to a solution, warmed to 130° C., of 19.2 g (0.05 mole) of 3,3-bis-(3'-tert.-butyl-4'-hydroxyphenyl)-butanoic acid and 0.05 g of KOH in 50 ml of dimethylformamide. Stirring is continued for four hours, a further 2 g of bisphenol A/F diglycidyl ether are then added and, after two hours, the solvent is distilled off in vacuo.

This gives a resin having a flowing point/dropping point of 107/118° C. Determination of the molecular mass gives a value of 1,965, which corresponds to a degree of oligomerization of 2.6.

EXAMPLE 7

Oligomer of

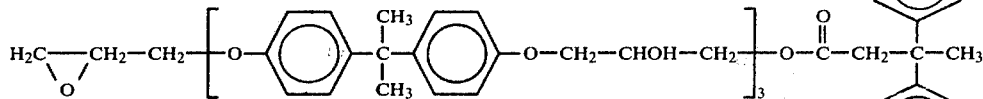
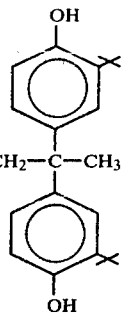

73.3 g (0.15 epoxy equivalent) of a commercial α,ω-diglycidyl ether of trimeric bisphenol A β-hydroxypropanediol ether in 200 ml of dimethylformamide are added dropwise, in the course of two hours and while blanketed with N₂, to a solution, warmed to 140° C., of 19.2 g (0.05 mole) of 3,3-bis-(3'-tert.-butyl-4'-hydroxyphenyl)-butanoic acid and a trace of KOH in 50 ml of dimethylformamide.

Stirring is then continued for six hours at 150° C. Removal of the solvent by distillation leaves a resin with a slight yellowish color and a flowing point/dropping point of 148/153° C. Determination of the molecular weight gave a value of 5,505, which corresponds to a degree of oligomerization of about 5.

EXAMPLES 8 to 15

Further polyepoxides were reacted analogously to the instructions given in Example 1 with 3,3-bis-(3'-tert.-butyl-4'-hydroxyphenyl)-butanoic acid (BBB) in the molar ratio indicated.

| Example No. | Polyepoxide | Moles of BBB per mole of polyepoxide | flowing point/ dropping point of the reaction product, °C. | Molecular weight |
|---|---|---|---|---|
| 8 | ![structure] | 1 | 144/149 | 6400 |

-continued

| Ex. ample No. | Polyepoxide | Moles of BBB per mole of polyepoxide | flowing point/ dropping point of the reaction product, °C. | Molecular weight |
|---|---|---|---|---|
| 9 | (tetrahydrophthalic acid diglycidyl ester) — structure with two $-C(=O)-O-CH_2-CH(-O-)CH_2$ groups on cyclohexene ring | 1 | 178/184 | — |
| 10 | $H_2C-CH-CH_2-O-CH_2-$ [bicyclic decalin-type ring system] $-CH_2-O-CH_2-CH-CH_2$ (with terminal epoxides) | 1 | 78/82 | — |
| 11 | $H_2C-CH-CH_2-O-(CH_2)_4-O-CH_2-CH-CH_2$ (with terminal epoxides) | 1 | 94/106 | 2160 |
| 12 | Triglycidyl isocyanurate: triazine ring with three $-N-CH_2-CH-CH_2$ (epoxide) substituents | 1.5 | 130/135 | 810 |
| 13 | $H_2C-CH-CH_2-O-$⟨C₆H₄⟩$-C(CH_3)_2-$⟨C₆H₄⟩$-O-CH_2-CH-CH_2$ (bisphenol A diglycidyl ether) | 1 | 86/93 | 750 |
| 14 | (3,4-epoxycyclohexyl)methyl 3,4-epoxycyclohexanecarboxylate: cyclohexene-oxide$-CH_2-O-C(=O)-$cyclohexene-oxide | 1 | 148/158 | 2710 |
| 15 | bis(epoxycyclohexylmethyl) adipate: epoxycyclohexyl-$CH_2-O-C(=O)-(CH_2)_4-C(=O)-O-CH_2-$epoxymethylcyclohexyl (with CH₃ groups) | 1 | 150/154 | 3830 |

EXAMPLES 16 to 34

Other phenolcarboxylic acids instead of BBB were reacted with polyepoxides analogously to Example 1, and the reaction was carried out without a solvent. The catalyst was a trace of 4-dimethylaminopyridine. 1 mole of polyepoxide was employed in each case.

| Example No. | Polyepoxide | moles of phenol-carboxylic acid | flowing point/ dropping point °C. |
|---|---|---|---|
| 16 | tetrahydrophthalic acid diglycidyl ester (as in Ex. 9, saturated cyclohexane version) | 1 of salicylic acid (2-HO-C₆H₄-COOH) | 88/99 |
| 17 | tetrahydrophthalic acid diglycidyl ester (cyclohexene version, as Ex. 9) | 1 " | 150/153 |
| 18 | $H_2C-CH-CH_2-O-$⟨C₆H₁₀⟩$-C(CH_3)_2-$⟨C₆H₁₀⟩$-O-CH_2-CH-CH_2$ (hydrogenated bisphenol A diglycidyl ether) | 1 " | 87/94 |

-continued

| Example No. | Polyepoxide | moles of phenol-carboxylic acid | flowing point/ dropping point °C. |
|---|---|---|---|
| 19 | cyclohexane-1,2-dicarboxylic acid bis(glycidyl) ester | 1 of HO—C₆H₂(tBu)₂—COOH | 128/130 |
| 20 | glycerol triglycidyl ether | 2 " | 72/76 |
| 21 | (3,4-epoxycyclohexyl)methyl 3,4-epoxycyclohexanecarboxylate | 1 of HO—C₆H₂(tBu)₂—CH₂—CH₂—COOH | 66/92 |
| 22 | bis[(3,4-epoxycyclohexyl)methyl] adipate | 1 of " | 60/67.5 |
| 23 | glycerol triglycidyl ether | 3 " | 124/128 |
| 24 | cyclohexane-1,2-dicarboxylic acid bis(glycidyl) ester | 1 " | 70/74 |
| 25 | " | 1 of " | 150 |
| 26 | triglycidyl isocyanurate | 1.5 " | 110/117 |
| 27 | cyclohexane-1,2-dicarboxylic acid bis(glycidyl) ester | 1 of HO—C₆H₂(tBu)₂—CH(COOH)—C₆H₂(tBu)₂—OH | 136/140 |
| 28 | bisphenol A diglycidyl ether | 1 of " | 103/109 |

-continued

| Example No. | Polyepoxide | moles of phenol-carboxylic acid | flowing point/ dropping point °C. |
|---|---|---|---|
| 29 | CH₂—O—CH₂—CH—CH₂ \\O/ <br> CH—O—CH₂—CH—CH₂ \\O/ <br> CH₂—O—CH₂—CH—CH₂ \\O/ | 1 " | 132/136 |
| 30 | " | 3 " | 119/123 |
| 31 | (cyclohexane-1,2-dicarboxylic acid bis(glycidyl ester)) | 1 of HO-Ar(di-tBu)-CH(—)-CH(CH₃)-COOH with second Ar(di-tBu)-OH | 129/142 |
| 32 | " | 1 of HO-Ar(di-tBu)-C(CH₃)(—)-CH₂-CH₂-COOH with second Ar(di-tBu)-OH | 136/140 |
| 33 | H₂C—CH—CH₂—O—Ar—C(CH₃)₂—Ar—O—CH₂—CH—CH₂ \\O/ ... \\O/ | 1 " | 87/92 |
| 34 | (cyclohexane-1,2-dicarboxylic acid bis(glycidyl ester)) | 1 of HO-Ar(di-tBu)-C(CH₃)(—)-CH₂-CH₂-CH₂-COOH with second Ar(di-tBu)-OH | 132/136 |

EXAMPLE 35

This example is intended to demonstrate the low volatility and stability to discoloration of the substances according to the invention.

These properties were tested by weighing out approximately 1 g of substance into a small weighing glass and then leaving the latter to stand, exposed to the atmosphere, for two hours in a heated cabinet at 200° C. The loss in weight determined is quoted as a percentage in the following table.

| Sample according to Example | Loss in weight in % |
|---|---|
| 1 | 0.28 |
| 4 | 0.47 |
| 5 | 0.68 |
| 8 | 0.20 |
| 10 | 0.33 |
| as a comparison: p-hydroxy-m,m'-di-tert.-butylphenylpropionic acid pentaerythritol ester | 0.74 |

Without exception, the products have only a slight yellow discoloration, corresponding to an iodine color number (as specified in DIN 6162) between 5 and 12.

EXAMPLE 36

This example shows the effectiveness of antioxidants according to the invention in a polypropylene wax having a molecular weight of 2,000 and a melt viscosity (measured at 170° C.) of 1,550 mPas, when the latter is exposed to heat.

0.5 g of the stabilizers according to the invention is added in each case to 100 g of wax, after which the mixture is stirred for five hours in a 250 ml three-necked flask at an internal temperature of 150° C., while simultaneously passing a stream of dry air through the mixture at 75 ml/minute and stirring with a loop stirrer at a speed of 200 r.p.m. The experiment is then discontinued. The melt viscosity of the samples is then determined at 170° C. with the aid of a rotational-type viscometer.

The values determined are shown in the following table.

| Substance according to Example No. | Melt viscosity at 170° C. (in mPas) |
|---|---|
| 1 | 984 |
| 5 | 1,100 |
| 11 | 776 |
| 26 | 1,171 |
| as a comparison: | |
| no stabilizer | 501 |
| commercially available stabilizer+ | 915 |

+3,3-bis-(3'-tert.-butyl-4'-hydroxyphenyl)-butanoic acid ethanediol diester

It can be seen from the table that the stabilizers according to the invention delay, in an impressive manner, the decline in viscosity caused by the action of heat and oxygen, and are comparable in this respect with commercially available, low-molecular phenol stabilizers.

EXAMPLE 37

The effectiveness of the stabilizers according to the invention as antioxidants is intended to be demonstrated in this example.

A mixture consisting of 100 parts by weight of unstabilized polypropylene powder having a density of 0.90 (melt index i5 approx. 6 g/10 minutes, determined by a method based on ASTM D 1238-62 T), 0.2 part by weight of calcium stearate and 0.3 part by weight of stabilizer is homogenized for five minutes at 200° C. on a twin-roll mill. The plastic melt is then compressed at 200° C. to give a sheet of 1 mm thickness. Test specimens in the form of a strip (100×10×1 mm) are then punched out of the plastic sheet. The resistance to heat-ageing of these specimens is determined by hanging them in a motor-driven frame with rotating trays in a circulating air drying cabinet and subjecting them to a temperature of 140° C. with a uniform inflow of fresh air. A record is made of the time after which an incipient local embrittlement occurs at certain places, which is characterized in accordance with DIN 53,383 by the formation of discolored, cloudy and in part crumbling areas. The test results are listed in the following table.

| Compound according to Example No. | Life (in days) |
|---|---|
| 1 | 25 |
| 8 | 23 |
| 9 | 28 |
| 18 | 34 |
| 19 | 21 |
| 20 | 35 |
| no stabilizer | 2 |
| commercially available stabilizer+ | 20 |

+ 3,3-bis-(3'-tert.-butyl-4'-hydroxyphenyl)-butanoic acid ethanediol diester

As can be seen from the table, the substances according to the invention are outstandingly suitable for stabilizing polyolefins.

We claim:

1. Epoxide derived compounds containing phenol groups and homo-oligomers thereof of the general formula (I)

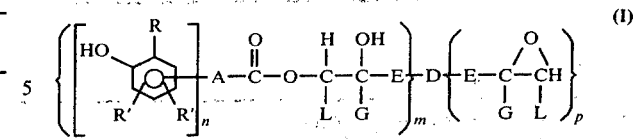

in which R is $C_1$ to $C_4$ alkyl, R' and R" independently of one another denote H or $C_1$ to $C_4$ alkyl, n is 1 or 2 and A is a chemical bond or (α) the radical of a straight-chain or branched, unsubstituted or phenyl-substituted alkane having 1 to 20 C atoms, or (β) the radical of a cycloaliphatic alkane which has 5 to 12 C atoms and is unsubstituted or substituted by $C_1$ to $C_5$ alkyl, or (γ) a phenyl or naphthyl radical unsubstituted or substituted by $C_1$ to $C_{12}$ alkyl, E represents a $CH_2$ group, G represents a H atom or a $CH_3$ group and L represents a H atom, or E and L conjointly with the C atoms linking them, form a cycloalkyl radical which has 5 to 12 C atoms and which can also be alkyl-substituted, and D is oxygen or a radical of the formula

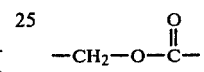

or

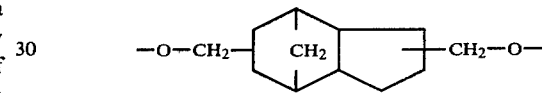

or $$-O-(CH_2)_q-O+CH_2-CHOH-CH_2-O-(CH_2)_q-O+_r-$$

or

in which M = ,

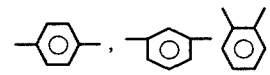

or

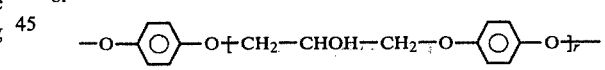

or

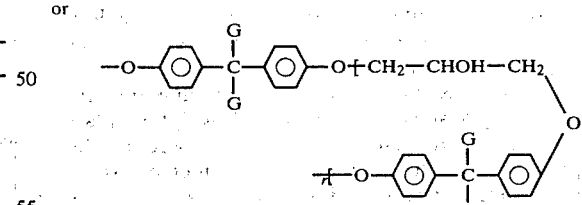

in which q = 2 to 10 and r = 0 to 10, or

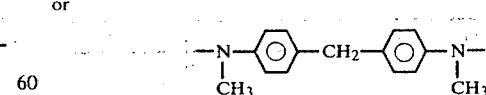

or

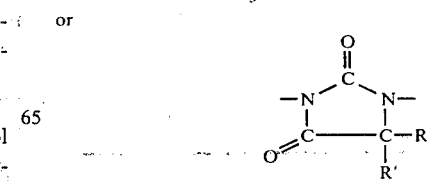

or

-continued

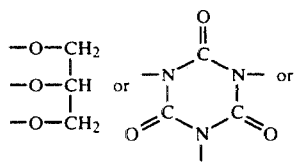

or

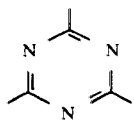

or

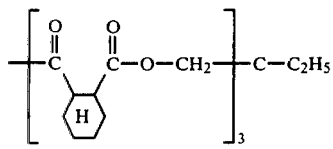

and m denotes 1, 2 or 3 and p denotes 0, 1 or 2, with the limitation that p+m is not greater than 3.

2. Process for the manufacture of compounds according to formula (I), characterized in that 0.01 to 1.0 mole of a phenolcarboxylic acid of the general formula (II)

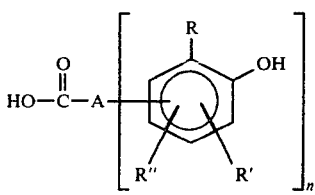

is reacted with one epoxide equivalent of a polyepoxide resin of the general structure (III)

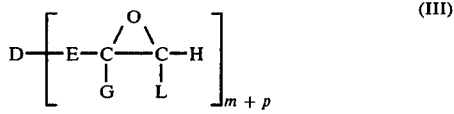

at 50° to 200° C., in the presence of an acid or basic catalyst and in the presence or absence of an inert solvent, the variable elements having the meaning indicated in claim 1.

3. A process for stabilizing homopolymers and copolymers formed from $C_2$ to $C_4$ $\alpha$-olefins against the harmful action of light and heat, which comprises adding on processing a compound of claim 1 in a quantity of 0.005 to 5.0 parts by weight on 100 parts by weight of polymer, suitably besides further light stabilizers and heat stabilizers.

4. Plastic compositions based on homopolymers and copolymers of $\alpha$-olefins having 2 to 4 C atoms, in which 0.005 to 5.0 parts by weight, relative to 100 parts by weight of polymer, of a compound according to claim 1 are present as a stabilizer against the harmful influence of heat and light.

* * * * *